(12) United States Patent
Gross

(10) Patent No.: US 6,716,998 B2
(45) Date of Patent: Apr. 6, 2004

(54) PROCESS FOR SYNTHESIS OF 2-YL CHROMAN DERIVATIVES

(75) Inventor: Jonathan L. Gross, Robbinsville, NJ (US)

(73) Assignee: Wyeth, Madison, NJ (US)

(*) Notice: Subject to any disclaimer, the term of this patent is extended or adjusted under 35 U.S.C. 154(b) by 0 days.

(21) Appl. No.: 10/264,528

(22) Filed: Oct. 4, 2002

(65) Prior Publication Data

US 2003/0100774 A1 May 29, 2003

Related U.S. Application Data

(60) Provisional application No. 60/327,417, filed on Oct. 5, 2001.

(51) Int. Cl.[7] ............... C07D 311/04; C07D 311/75
(52) U.S. Cl. ............... 549/398; 549/399; 549/405
(58) Field of Search ................ 549/398, 399, 549/405

(56) References Cited

U.S. PATENT DOCUMENTS

| 4,424,389 A | 1/1984 | Sakito |
| 5,318,988 A | 6/1994 | Schohe-Loop et al. |
| 5,371,094 A | 12/1994 | Heine et al. |

FOREIGN PATENT DOCUMENTS

| GB | 1 590 938 | 6/1981 |
| JP | 08238095 | 9/1996 |
| WO | WO 02/20507 A1 | 3/2002 |

OTHER PUBLICATIONS

P. Bravo et al., J. Heterocyclic Chem., 15, 1051–1053 (1978).
J.Y. Goujon et al., Synlett, 2, 322–324 (2002).
S. Bouzbouz et al., Eur. J. Org. Chem., 3223–3228 (2000).
F. M. Dean et al., Tetrahedron Letters, 24(24), 2495–2496 (1983).
U.S. patent application Ser. No. 10/264,947, Stack et al.
Mitsunobu, Synthesis, 1–27 (1981).
Goujon et al., J. Chem. Soc., Perkin Trans., 1, 496–499 (2002).
Chang et al., J. Org. Chem., 63, 864–866 (1998).
Grubbs et al., Tetrahedron 54, 4413–4450 (1998).
Achinami Kazuo, Patent Abstracts of Japan, vol. 1997, No. 1.

*Primary Examiner*—Alan L. Rotman
*Assistant Examiner*—Raymond Covington
(74) *Attorney, Agent, or Firm*—Kimberly R. Hild

(57) ABSTRACT

This invention provides a process for the stereospecific preparation of 2-yl-chroman and -chromene derivatives of the formula:

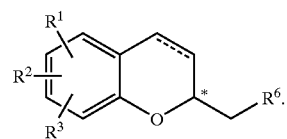

These compounds are useful for the preparation of optically active 2-aminomethyl- and 2-azaheterocyclylmethyl-chromans.

23 Claims, No Drawings

PROCESS FOR SYNTHESIS OF 2-YL CHROMAN DERIVATIVES

CROSS REFERENCE TO RELATED APPLICATIONS

This application claims the benefit under 35 U.S.C. §119(e) to U.S. provisional application Ser. No. 60/327,417 filed Oct. 5, 2001, which is hereby incorporated by reference in its entirety.

FIELD OF THE INVENTION

The present invention relates to a stereospecific process for the preparation of 2-yl-chroman and -chromene derivatives.

BACKGROUND OF THE INVENTION

Various 2-yl-chroman and -chromene derivatives have been used as intermediates in the synthesis of various agents such as medicinal agents. For example, U.S. Pat. No. 5,371,094 discloses the use of 2-ylmethyl chroman derivatives in the preparation of a series of azaheterocyclylmethyl-chromans that are useful for controlling diseases of the central nervous system. Also, for example, U.S. Pat. No. 5,318,988 discloses the use of 2-ylmethyl chroman derivatives of the formulae:

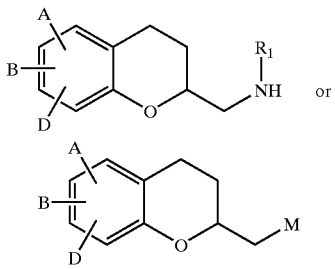

for preparing compounds having the formula

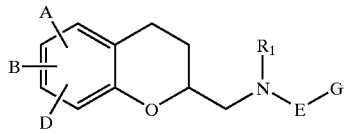

where M represents a typical leaving group such as chloride, bromide, iodide, tosylate, mesylate or triflate, E represents a direct bond or an alkylene or alkenylene having in each case up to 10 carbon atoms, which are optionally substituted by phenyl, G represents an optionally substituted cyclic or heterocyclic moiety containing one or more rings. These compounds are disclosed as being useful for combating disease of the central nervous system.

The processes disclosed in these patents for making chroman derivatives are nonstereoselective necessitating separation of the diastereomers into their single stereoisomeric constituents through conventional methods. It would be desirable to provide processes for the efficient production of 2-yl chroman and chromene derivatives that are stereoselective and more preferably stereospecific.

Processes for making 2-yl chroman and chromene derivatives in a nonstereoselective manner are known. S. Chang and R. H. Grubbs, *J. Org. Chem.*, Vol. 63, pp. 864–866 (1998), describe the synthesis of certain chromene derivatives from styrenyl allyl ether dienes using catalytic ring-closing olefin metathesis.

It would be desirable to provide a stereospecific process for producing 2-yl chroman and chromene derivatives.

SUMMARY OF THE INVENTION

The present invention provides a stereospecific process for preparing 2-yl chromene derivatives that includes:
(a) reacting a 2-hydroxy substituted styrene of formula (I)

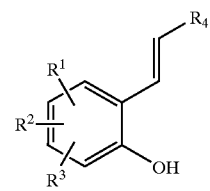

and an optically active 3-hydroxy-1-butene of formula (II)

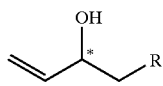

to form an optically active diene of formula (III)

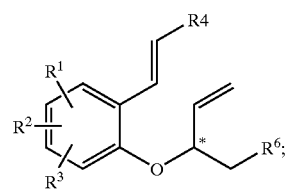

wherein R is a leaving group or a protected oxygen group,
wherein $R^1$, $R^2$ and $R^3$ are independently selected from hydrogen, a halogen atom, a cyano, azido, nitro, hydroxyl, carboxyl, acyl or carboxamido group, a $C_1$ to $C_6$ alkyl group, a 5- to 7-membered aromatic group optionally having as ring members up to 2 heteroatoms independently selected from O, N or S, a $C_5$ to $C_7$ membered aryloxy group, a $C_1$ to $C_6$ alkoxy group, alkanamido group having 1 to 6 carbon atoms in the alkyl chain, alkanesulfonamido group having 1 to 6 carbon atoms in the alkyl chain, an alkanoyloxy group having 1 to 6 carbon atoms in the alkyl chain, a perhalogenated $C_1$ to $C_6$ alkyl or alkoxy group, an amino group or a mono- or di-alkylamino having 1 to 6 carbon atoms per alkyl chain, or two of $R^1$, $R^2$ or $R^3$, taken together, form a 5- to 7-membered saturated or aromatic carbocyclic or bridged carbocyclic ring, wherein the ring may i) optionally have up to two ring atoms selected from S, N, or O, ii) optionally have as a ring member up to 2 carbonyl groups or iii) optionally be substituted by 1 to 2 $R^5$ substituents where each $R^5$ substituent is independently selected from a halogen atom, a cyano, nitro or hydroxyl group, a $C_1$–$C_6$ alkyl group, a $C_1$–$C_6$ alkoxy group, a $C_3$–$C_6$ cycloalkyl group, a 5- to 7-membered aromatic group optionally having 1–2 ring atoms selected from N, O or S, or in Spiro form a carbocyclic ring having 5 to 7 carbon atoms, or any combination of i), ii), or iii),
wherein $R^4$ is H or a $C_1$ to $C_6$ alkyl group, and
wherein $R^6$ is a hydroxyl group, a protected oxygen group, or a leaving group; and (b) subjecting the diene of formula (III) to a ring closing metathesis polymerization reaction in the presence of a catalyst to stereospecifically produce an optically active 2-yl chromene derivative of formula (IV)

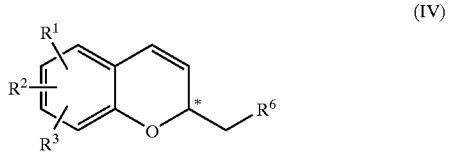

(IV)

where $R^1$, $R^2$, $R^3$ and $R^6$ are defined as in formula (III).

The invention further includes a process for producing a 2-yl chroman by hydrogenating the 2-yl chromene, as well as a process for making the hydroxy substituted styrene of formula (I).

DETAILED DESCRIPTION OF THE INVENTION

The present invention is directed to a stereospecific process for preparing 2-yl chroman and chromene derivatives of the formula:

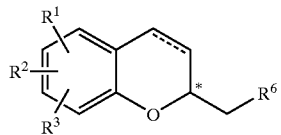

where:
$R^1$, $R^2$ and $R^3$ are independently selected from hydrogen, a halogen atom, or a cyano, azido, nitro, hydroxyl, carboxyl, acyl or carboxamido group, a $C_1$ to $C_6$ alkyl group, a 5- to 7-membered aromatic group optionally having as ring members up to 2 heteroatoms independently selected from O, N or S, a $C_5$ to $C_7$ membered aryloxy group, a $C_1$ to $C_6$ alkoxy group, a $C_2$ to $C_7$ alkenyl group, a carboalkoxy group having 1 to 6 carbon atoms in the alkyl chain, alkanamido group having 1 to 6 carbon atoms in the alkyl chain, alkanesulfonamido group having 1 to 6 carbon atoms in the alkyl chain, an alkanoyloxy group having 1 to 6 carbon atoms in the alkyl chain, a perhalogenated $C_1$ to $C_6$ alkyl or alkoxy group such as a trifluoromethyl or trifluoromethoxy group, an amino group, or a mono- or di-alkylamino group having 1 to 6 carbon atoms per alkyl chain, or two of $R^1$, $R^2$ or $R^3$, taken together, form a 5- to 7-membered saturated, partly saturated, unsaturated, or aromatic carbocyclic or bridged carbocyclic ring, where the ring may i) optionally have up to two ring atoms selected from S, N, or O, ii) optionally have as a ring member up to 2 carbonyl groups or iii) be optionally substituted by 1 to 2 $R^5$ substituents, where each $R^5$ substituent is independently selected from a halogen atom, a cyano, nitro or hydroxyl group, a $C_1$–$C_6$ alkyl group, a $C_1$–$C_6$ alkoxy group, a $C_3$–$C_6$ cycloalkyl group, a 5- to 7-membered aromatic group optionally having 1–2 ring atoms selected from N, O or S, or in spiro form a carbocyclic ring having 5 to 7 carbon atoms, or any combination of i), ii), or iii); and
$R^6$ is a hydroxyl group, a protected oxygen group or a leaving group.

By "stereospecific" as used herein, it is meant a reaction where starting materials differing only in their spacial configuration are converted to stereoisomerically distinct products. For example, in a stereospecific reaction, if the starting material is enantiopure (100% enantiomer excess "ee"), the final product will also be enantiopure. Similarly if the starting material has an enantiomer excess of about 50%, the final product will also have about a 50% enantiomer excess. "Enantiomer excess" as used herein refers to the mole percent excess of a single enantiomer over the racemate.

By "optically active" as used herein, it is meant a non-racemic mixture of chiral molecules. The "*" in the formulas indicates the chiral carbon providing the optical activity.

The process of the present invention preferably produces 2-yl chromene and chroman derivatives having an enantiomer excess of at least about 30%, more more preferably at least about 50%, and most preferably at least about 95%. In the most preferred embodiment of the present invention, enantiopure 2-yl chromene and chroman derivatives are produced.

As used herein, unless otherwise indicated, any moiety containing an alkyl or alkenyl group such as for example, an alkyl, alkane, alkenyl, alkoxy, carboalkoxy, or alkanamido group, may be branched or straight chained and contain up to 7 carbon atoms in the alkyl/alkenyl chain. Alkenyl groups, unless otherwise, indicated may be monounsaturated, polyunsaturated or fully unsaturated. Cycloalkyl means a carbocyclic ring having 3–8 carbon atoms. Aromatic and aryl mean an aromatic 5- to 7-membered carbocyclic ring such as phenyl. Heteroaromatic and heteroaryl mean an aromatic 5- to 7-membered ring having one or two heteroatoms which independently may be N, O, or S. Acyl means an alkanoyl group having 2 to 7 carbon atoms. Any moiety containing an alkyl, alkenyl, cycloalkyl aromatic, heteroaromatic, aryl, or heteroaryl group may optionally be substituted as defined hereinafter. For example, alkyl moieties may be halogenated, such as mono- or difluoromethyl or mono- or difluoromethoxy. Halogen means fluorine, chlorine, bromine or iodine.

The term "substituted" as used herein refers to a moiety, such as an aryl or akyl moiety having from 1 to about 5 substituents, and more preferably from 1 to about 3 substituents independently selected from halogen atom, a cyano, nitro or hydroxyl group, a $C_1$–$C_6$ alkyl group, a $C_1$–$C_6$ alkoxy group, a $C_3$–$C_6$ cycloalkyl group, a 5- to 7-membered aromatic group optionally having 1–2 ring atoms selected from N, O or S, or in spiro form a carbocyclic ring having 5 to 7 carbon atoms. Preferred substituents are halogen atom, a cyano, nitro or hydroxyl group, a $C_1$–$C_6$ alkyl group, or a $C_1$–$C_6$ alkoxy group.

The term "leaving group" as used herein refers to any moiety or atom that is susceptible to nucleophilic substitution or elimination. Typically, these are atoms or moieties that when removed by nucleophilic substitution or elimination are stable in anionic form. Examples of leaving groups useful in the present invention include alkyl or arylsulphonate groups such as tosylate, brosylate, mesylate or nosylate, or halides such as chloride, bromide, or iodide. Tosylate, or 4-methylbenzenesulfonate, is an especially preferred leaving group in the practice of this invention.

The term "protected oxygen group" as used herein refers to an —$OR^7$ moiety, where $R^7$ is an oxygen protecting moiety that is relatively inert to reaction conditions under which alcohols normally react, such as under Mitsunobu reaction conditions. Examples of preferred $R^7$ moieties useful in the present invention include alkyl groups; aryl groups such as benzyl or 2-nitrobenzyl; or silyl groups such as t-butyldimethylsilyl or triethylsilyl to form the corresponding ether as the protected oxygen group. Also, $R^7$ may be, for example, aryl or alkyl carbonyl moieties to form aryl or alkyl esters as the protected oxygen group, such as acetate or pivaloate. One skilled in the art will be able to identify other suitable oxygen protecting groups such as those described in T. W. Green and P. G. M. Wuts: *Protective Groups in Organic Synthesis*, Second Edition (Wiley, NY, 1991), the disclosure of which is hereby incorporated by reference in its entirety.

The process of this invention provides an efficient route to the synthesis of 2-yl chroman and chromene derivatives. For example the processes of the present invention preferably provide 2-yl chroman and chromene derivatives in enantiomer excess. Thus, subsequent resolution and/or purification steps may not be needed to isolate a single enantiomer.

In one embodiment of the present invention, 2-yl chroman and chromene derivatives can be produced according to reaction Scheme (I).

SCHEME I

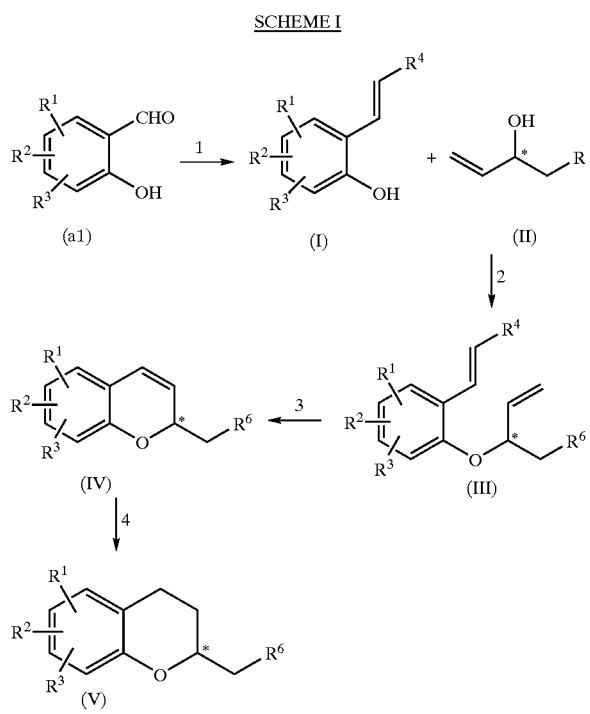

Referring to Scheme I, in step 1, a salicylaldehyde, as shown, is olefinated to produce a 2-hydroxy substituted styrene compound of formula (I), where $R^4$ is hydrogen or a $C_1$ to $C_6$ alkyl group (such as methyl). In this reaction scheme, preferably $R^4$ is hydrogen. This olefination may be accomplished by any suitable method known to those skilled in the art such as under Wittig reaction conditions. In a preferred embodiment, the olefination of step 1 may be accomplished by treatment of the salicylaldehyde with an ylide derived from the reaction of methyltriphenylphoshonium bromide and butyllithium.

In step 2, the resulting 2-hydroxy styrene compound is reacted with an optically active 3-hydroxy-1-butene compound of formula (II) to form a diene of formula (III). In a preferred embodiment of the present invention, R of the 3-hydroxy-1-butene compound is a protected oxygen group "OR$^7$" to provide a 3-butene-1,2-diol having the following formula:

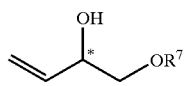

where $R^7$ is as previously defined herein. The optically active 3-hydroxy-1-butene compound of formula (II) is commercially available and can be obtained for example from Acros Organics Catalog, supplied by Acros Organics N.V., located in Fairlawn, N.J. Alternatively, it can be synthesized according to methods disclosed in for example EP 0 561 321 A2, the disclosure of which is hereby incorporated by reference in its entirety. Preferably, the optically active 3-hydroxy-1-butene compound of formula (II) used has an enantiomer excess of at least about 30%, more preferably at least about 50% and most preferably at least about 95%. In a most preferred embodiment an enantiopure 3-hydroxy-1-butene compound of formula (II) is used.

The reaction in step 2 involves a stereospecific dehydration reaction of the 2-hydroxy group of the styrene compound with the secondary alcohol of the butene compound. In a preferred embodiment, the reaction of step 2 is performed under Mitsunobu reaction conditions, such as for example, in the presence of triphenylphosphine and diethylazodicarboxylate. The Mitsunobu reaction proceeds in a stereospecific manner with net inversion of configuration at the stereogenic center containing the secondary alcohol. The use of an optically active 3-hydroxy-1-butene compound of formula (II), therefore, allows for the predictable and reliable incorporation of stereochemical information and results in being able to produce an optically active 2-yl chromene or chroman derivative that has a percent enantiomer excess corresponding to the percent enantiomer excess of the 3-hydroxy-1-butene compound. One skilled in the art will recognize other suitable reaction conditions for performing this stereospecific dehydration reaction. For example, the articles by Mitsunobu, *The Use of Diethyl Azocicarboxylate and Triphenylphosphine in Synthesis and Transformation of Natural Products*, Synthesis, pages 1 to 28, (1981); and J. Dodge, et al., *Advances In The Mitsunobu Reaction For The Stereochemical Inversion Of Hindered Secondary Alcohols*, Recent Research Developments in Organic Chemistry (1) p. 273–283 (1997) provide many other suitable reaction conditions. The disclosure of these two articles is hereby incorporated by reference in their entireties.

In step 3, the diene of formula (III) is subjected to a ring closing metathesis (RCM) polymerization reaction to stereospecifically form a 2-yl chromene derivative of formula (IV). Optionally, as indicated by the $R^6$ substituent on the diene of formula (III), the protected oxygen group or leaving group "R" on the 3-hydroxy-1-butene compound may be converted to a hydroxyl group using conventional techniques, any time after the dehydration reaction of step 2.

The ring closing metathesis reaction is conducted in the presence of a catalyst, such as bis(tricyclopentylphosphine) benzylidine ruthenium (IV) dichloride. Other suitable catalysts include for example metal carbene complexes such as those based on titanium, tungsten, molybdenum, or ruthenium. Mo complexes such as alkoxy imido molybdenum complexes and other ruthenium carbene complexes disclosed for example in Grubbs et al., *Recent Advances in Olefin Metathesis and its Application in Organic Synthesis*, Tetrahedron (54) p. 4413–4450 (1998) are more preferred. One skilled in the art will recognize that the ring closing metathesis reaction can be performed under a variety of reaction conditions. For example, a variety of different catalysts, reaction solvents, reaction temperatures and reaction times may be used. For a more complete description of suitable reaction conditions for performing the ring closing metathesis reaction useful in this invention, see e.g., Grubbs et al., *Recent Advances in Olefin Metathesis and its Application in Organic Synthesis*, Tetrahedron (54) p. 4413–4450 (1998) and Ivin et al., Olefin Metathesis and metathesis Polymerization, Academic Press, Sandiego (1997). The disclosures of these documents are hereby incorporated by reference in their entirety.

In step 4, the double bond of the 2-yl chromene derivative is reduced to produce the corresponding 2-yl chroman derivative of formula (V). Reduction of the double bond may be accomplished by any suitable method known to those skilled in the art. For example, reduction may be carried out via hydrogenation of the double bond in ethanol and in the presence of a palladium catalyst.

In another embodiment of the present invention, 2-yl chroman and chromene derivatives can be produced according to reaction Scheme (II).

diphenyl ether or mesitylene. In a preferred embodiment, the refluxing is carried out using mesitylene.

In step 3, the terminal double bond of the phenol compound of formula (c2) is then isomerized using conventional techniques to form a 2-hydroxy styrene compound of formula (I), where R4 is methyl (i.e., 2-[2-propenyl]phenol). Preferably, isomerization of the double bond is done in the presence of a palladium catalyst such as bis(acetonitrile) dichloropalladium (II).

Steps 4, 5, and 6 of Scheme II are carried out in accordance with the procedures described for Steps 2, 3, and 4, respectively, of Scheme I. In this regard, the 2-hydroxy styrene compound of formula (I) is reacted with an optically active 3-hydroxy-1-butene of formula (II) to form a diene of formula (III). A ring closing metathesis reaction is then performed on the diene to yield a 2-yl chromene of formula (IV). The double bond of the 2-yl chromene derivative may then be hydrogenated to form the corresponding 2-yl chroman derivative of formula (V).

SCHEME II

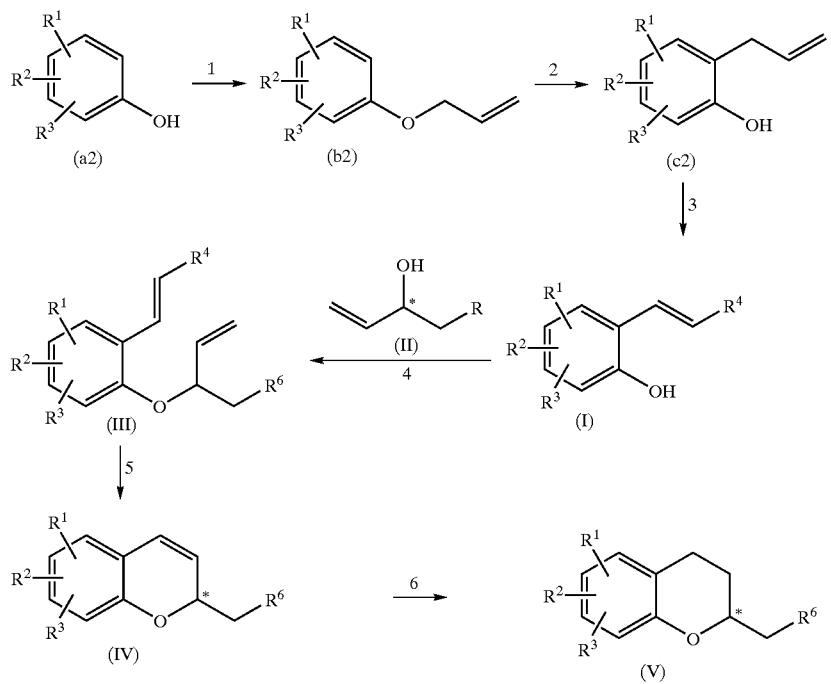

In the embodiment illustrated in Scheme II, a phenol of formula (a2) is reacted with an allyl halide such as allyl bromide in the presence of a suitable base such as an alkali metal or alkaline earth metal hydride or an alkali metal carbonate such as sodium hydride or potassium carbonate to form an allyl ether of formula (b2). In a preferred embodiment the base is potassium carbonate. One skilled in the art will recognize that the allylation can be carried out under a variety of reaction conditions. In a preferred embodiment, the allylation is conducted using allyl bromide in the presence of potassium carbonate.

In step 2 of scheme 2, the allyl ether of formula (b2) is rearranged under Claissen rearrangement reaction conditions to provide the phenol compound of formula (c2). Preferably, the Claisen rearrangement is carried out by heating the allyl ether of formula (b2) under reflux using a suitable organic solvent preferably having a boiling point ranging from about 170° C. to about 250° C. such as One skilled in the art, in reading the above, will readily recognize that where catalysts or solvents are included in a reaction step of the process of the present invention, it is expected that other catalysts or solvents known in the art, but not mentioned herein, may be used. Moreover, those skilled in the art will recognize that the reactions disclosed herein, such as the dehydration of the 2-hydroxy styrene compound of formula (I) with the 3-hydroxy-1-butene compound of formula (II), the ring closing metathesis reaction of the diene of formula (III), and the hydrogenation of the 2-yl chromene of formula (IV) can be performed under a variety of reaction conditions using the teachings herein in combination with the knowledge available to those skilled in the art. For example, various reaction temperatures, pressures, solvents, catalysts and equipment can be used in accordance with the process of the present invention. It is also contemplated for example, that although the processes described in the examples are batch, they could be adapted to for semicontinuous or continuous operations.

Thus, variations in the specific methods of accomplishing individual steps of the invention will be apparent to those in the art. Although all these possible variations cannot be set forth herein, such variations are contemplated to be within the scope of the present invention.

The process of this invention preferably permits the stereospecific synthesis of 2-yl-chromans. The concise nature of the reaction sequence, ease of synthesis, and abundance of potential starting materials makes this process a practical method for the preparation of optically active 2-yl chroman and chromene derivatives.

As previously mentioned, the 2-yl chroman and chromene derivatives can be further reacted to prepare a variety of useful medicinal agents. For example, the 2-yl chroman and chromene derivatives can be further reacted to form 2-aminomethyl- or 2-azaheterocyclylmethyl-chroman compounds, which are useful in the treatment of diseases of the central nervous system. Methods to synthesize these chromans are disclosed in for example U.S. Pat. Nos. 5,371,094, and 5,318,988, the disclosures of which are hereby incorporated by reference in their entireties.

EXAMPLES

The following Examples illustrate specific embodiments of the process of the present invention, but should not be construed as limiting the scope of the invention.

Example 1 a) (2R)-2-{2-[1-propenyl]phenoxy}-3-butenyl 4-methylbenzenesulfonate

To a solution of 2-[1-propenyl]phenol (3.00 g, 22.4 mmol) in toluene (200 mL) cooled to 0° C. is added (S)-2-hydroxy-3-buten-1-yl p-tosylate (8.12 g, 33.5 mmol) and triphenylphosphine (9.24 g, 35.2 mmol), followed by dropwise addition of diethyl azodicarboxylate (6.13 g, 35.2 mmol), and the reaction mixture is allowed to stir at room temperature for 12 hours. The reaction mixture is then quenched by the addition of water (200 mL). The aqueous layer is separated and extracted with diethyl ether (2×200 mL). The combined organic extracts are washed with water (200 mL) and aqueous sodium chloride (300 mL), dried (magnesium sulfate), and the solvent is removed in vacuo to give a crude solid. Purification by flash column chromatography (silica, ethyl acetate:hexanes 3:7) provides 5.17 g (64% y, >97% ee) of (2R)-2-{2-[1-propenyl]phenoxy}-3-butenyl 4-methylbenzenesulfonate as a colorless oil. $[\alpha]_D^{25}$=−15.0 (c 6.6 in methanol, >97% ee); $R_f$=0.47 (silica, ethyl acetate:hexanes 3:7); Anal. Calcd. for $C_{20}H_{22}O_4S$: C, 67.02; H, 6.19. Found: C, 67.56; H, 6.25.

b) (2R)-2H-chromen-2-ylmethyl 4-methylbenzenesulfonate

To a solution of (2R)-2-{2-[1-propenyl]phenoxy}-3-butenyl 4-methyl-benzenesulfonate (3.61 g, 10.1 mmol) in dichloromethane (100 mL) is added bis(tricyclopentylphosphine)benzylidene ruthenium (IV) dichloride (1.49 g, 2.01 mmol) and the reaction mixture is stirred at room temperature for 16 hours. The solvent is removed in vacuo to give a crude solid. Purification by flash column chromatography (silica, ethyl acetate:hexanes 3:7) provides 2.48 g (78% y, >97% ee) of (2R)-2H-chromen-2-ylmethyl 4-methylbenzenesulfonate as a pale green crystalline solid. $[\alpha]_D^{25}$=+175.12 (c 9.99 in methanol, >97% ee); $R_f$=0.40 (silica, ethyl acetate:hexanes 3:7); Anal. Calcd. for $C_{17}H_{16}O_4S$: C, 64.54; H, 5.10. Found: C, 64.85; H, 5.05.

c) (2R)-3,4-dihydro-2H-chromen-2-yl methyl 4-methylbenzenesulfonate

To a solution of (2R)-2H-chromen-2-ylmethyl 4-methylbenzenesulfonate (1.70 g, 55.00 mmol) in ethanol (100 mL) is added palladium on carbon (10 wt. %, 0.17 g) and the reaction mixture is shaken under an H2 atmosphere (50 psi) for 6 hours. The reaction mixture is filtered (celite) and the solvent removed in vacuo to provide (2R)-3,4-dihydro-2H-chromen-2-ylmethyl 4-methylbenzenesulfonate (1.62 g, 95%) as a colorless oil which crystallizes upon standing. $[\alpha]_D^{25}$=−52.69 (c 10.06 in methanol, >97% ee); $R_f$=0.60 (silica, ethyl acetate:hexanes 2:3); Anal. Calcd. for $C_{17}H_{18}O_4S$: C, 64.13; H, 5.70. Found: C, 63.90; H, 5.71.

Example 2 a) (2R)-2-(2-methoxy-6-vinylphenoxy)-3-butenyl-4-methylbenzenesulfonate

To a suspension of methyltriphenylphosphonium bromide (19.65 g, 55.00 mmol) in tetrahydrofuran (200 mL) cooled to 0° C. is added n-butyllithium (1.6 M in hexanes, 37.5 mL, 60.00 mmol) and the reaction mixture is allowed to stir at 0° C. for 30 min. The ylide is added via cannula to a solution of 3-methoxysalicylaldehyde (3.80 g, 25.00 mmol) in tetrahydrofuran (100 mL) and the reaction mixture is allowed to stir at room temperature for 3 hours. The reaction mixture is quenched by the addition of aqueous ammonium chloride (100 mL) and diluted with water (300 mL). The aqueous layer is separated and extracted with diethyl ether (3×200 mL). The combined organic extracts are washed with water (300 mL) and aqueous sodium chloride (300 mL), dried (magnesium sulfate), and filtered through a plug of silica (10 cm×5 cm). The solvent is removed in vacuo to give the 2-vinylphenol as a crude oil which is dissolved in tetrahydrofuran (200 mL). To the resulting solution is added (S)-2-hydroxy-3-buten-1-yl p-tosylate (7.27 g, 30.00 mmol), triphenylphosphine (7.87 g, 30.00 mmol), and diethyl azodicarboxylate (5.22 g, 30.00 mmol). The reaction mixture is allowed to stir at room temperature for 12 hours. The reaction mixture is quenched by the addition of water (200 mL). The aqueous layer is separated and extracted with ethyl acetate (2×250 mL). The combined organic extracts are washed with water (200 mL) and aqueous sodium chloride (300 mL), dried using magnesium sulfate, and the solvent is removed in vacuo to give a crude solid. Purification by flash column chromatography (silica, ethyl acetate:hexanes 4:1) provides 5.33 g (57% y, >97% ee) of (2R)-2-(2-methoxy-6-vinylphenoxy)-3-butenyl 4-methylbenzenesulfonate as a colorless oil. $[\alpha]_D^{25}$=−8.06 (c 9.93 in chloroform, >97% ee); $R_f$=0.57 (silica, ethyl acetate:hexanes 3:7); Anal. Calcd. for $C_{20}H_{22}O_5S\cdot0.2H_2O$: C, 63.57; H, 5.97. Found: C, 63.37; H, 5.66.

b) [(2R)-8-methoxy-2H-chromen-2-yl]methyl-4-methylbenzenesulfonate

To a solution of (2R)-2-(2-methoxy-6-vinylphenoxy)-3-butenyl-4-methylbenzenesulfonate (3.00 g, 8.01 mmol) in dichloromethane (100 mL) is added bis(tricyclopentylphosphine)benzylidene ruthenium (IV) dichloride (0.59 g, 0.80 mmol) and the reaction mixture is stirred at room temperature for 4 hours. The solvent is removed in vacuo to give a crude solid. Purification by flash column chromatography (silica, ethyl acetate:hexanes 2:3) provides 2.47 g (68% y, >97% ee) of [(2R)-8-methoxy-2H-chromen-2-yl]methyl 4-methylbenzenesulfonate as a light purple oil. $[\alpha]_D^{25}$=+150.31 (c 10.18 in chloroform, >97% ee); $R_f$=0.53 (silica, ethyl acetate:hexanes 2:3); Anal. Calcd. for $C_{18}H_{18}O_5S\cdot0.2H_2O$: C, 61.77; H, 5.29. Found: C, 61.49; H, 5.00.

Example 3 a) 4-(allyloxy)-1-[(4-methylphenyl)sulfonyl]-1H-indole

Treatment of 1-[(4-methylphenyl)sulfonyl]-1H-indol-4-ol with potassium carbonate and allyl bromide in N,N- dimethylformamide (29.24 g, 0.242 mol) followed by aqueous workup and extraction with diethyl ether provides 4-(allyloxy)-1-[(4-methylphenyl)sulfonyl]-1H-indole.

b) 5-allyl-1-[(4-methylphenyl)sulfonyl]-1H-indol-4-ol

Refluxing a solution of 4-(allyloxy)-1-[(4-methylphenyl) sulfonyl]-1H-indole in mesitylene followed by removal of the solvent and subsequent purification by flash column chromatography provides 5-allyl-1-[(4-methylphenyl) sulfonyl]-1H-indol-4-ol.

c) 1-[(4-methylphenyl)sulfonyl]-5-[(1E)-prop-1-enyl]-1H-indol-4-ol

Treatment of a refluxing solution of 5-allyl-1-[(4-methylphenyl)sulfonyl]-1H-indol-4-ol in dichloromethane with bis(acetonitrile)dichloropalladium (II) followed by removal of the solvent and subsequent purification by flash column chromatography gives 1-[(4-methylphenyl) sulfonyl]-5-[(1E)-prop-1-enyl]-1H-indol-4-ol.

d) (2R)-2-({1-[(4-methylphenyl)sulfonyl]-5-[(1E)-prop-1-enyl]-1H-indol-4-yl}oxy)but-3-enyl 4-methylbenzenesulfonate Treatment of 1-[(4-methylphenyl)sulfonyl]-5-[(1E)-prop-1-enyl]-1H-indol-4-ol with (S)-2-hydroxy-3-buten-1-yl p-tosylate, triphenylphosphine, and diethylazodicarboxylate in toluene following the procedure described for Example 1a affords (2R)-2-({1-[(4-methylphenyl)sulfonyl]-5-[(1E)-prop-1-enyl]-1H-indol-4-yl}oxy)but-3-enyl 4-methylbenzenesulfonate.

e) {(2-7-[(4-methylphenyl)sulfonyl]-2,7-dihydropyrano[2,3-e]indol-2-yl}methyl 4-methylbenzenesulfonate Treatment of (2R)-2-({1-[(4-methylphenyl)sulfonyl]-5-[(1E)-prop-1-enyl]-1H-indol-4-yl}oxy)but-3-enyl 4-methylbenzenesulfonate with bis(tricyclopentylphosphine) benzylidene ruthenium (IV) in dichloromethane under the conditions described for Example 1b gives {(2R)-7-[(4-methylphenyl)sulfonyl]-2,7-dihydropyrano[2,3-e] indol-2-yl}methyl 4-methylbenzenesulfonate.

f) {(2R)-7-[(4-methylphenyl)sulfonyl]-2,3,4,7-tetrahydropyrano[2,3-e]indol-2-yl}methyl 4-methylbenzenesulfonate Treatment of {(2R)-7-[(4-methylphenyl)sulfonyl]-2,7-dihydropyrano[2,3-e]indol-2-yl}methyl 4-methylbenzenesulfonate with palladium on carbon (10 wt. %) in ethanol following the procedure described for Example 1c gives {(2R)-7-[(4-methylphenyl)sulfonyl]-2,3,4,7-tetrahydropyrano[2,3-e]indol-2-yl}methyl 4-methylbenzenesulfonate.

Example 4 a) 6-[(1E)-prop-1-enyl]quinolin-5-ol

Treatment of 6-allylquinolin-5-ol in dichloromethane with bis(acetonitrile)dichloropalladium (II) following the procedure described for Example 3c affords 6-[(1E)-prop-1-enyl]quinolin-5-ol.

b) 2-({6-[(1E)-prop-1-enyl]quinolin-5-yl}oxy)but-3-enyl 4-methylbenzenesulfonate Treatment of 6-[(1E)-prop-1-enyl]quinolin-5-ol with (S)-2-hydroxy-3-buten-1-yl p-tosylate, triphenylphosphine, and diethylazodicarboxylate in toluene following the procedure described for Example 1a provides 2-({6-[(1E)-prop-1-enyl] quinolin-5-yl}oxy)but-3-enyl 4-methylbenzenesulfonate.

c) 2H-pyrano[2,3-]quinolin-2-ylmethyl 4-methylbenzenesulfonate

Treatment of 2-({6-[(1E)-prop-1-enyl]quinolin-5-yl}oxy) but-3-enyl 4-methylbenzenesulfonate in dichloromethane with bis(tricyclopentylphosphine) benzylidene ruthenium (IV) under the conditions described for Example 1b provides 2H-pyrano[2,3-]quinolin-2-ylmethyl 4-methylbenzenesulfonate.

d) 3,4-dihydro-2H-pyrano[2,3-f]quinolin-2-ylmethyl 4-methylbenzenesulfonate

Treatment of 2H-pyrano[2,3-f]quinolin-2-yl-methyl 4-methylbenzene-sulfonate with palladium on carbon (10 wt. %) in ethanol following the procedure described for Example 1c affords 3,4-dihydro-2H-pyrano[2,3-f]quinolin-2-ylmethyl 4-methylbenzenesulfonate.

Example 5 a) 2-[(2-vinyl-1-naphthyl)oxy]but-3-enyl 4-methylbenzenesulfonate

Treatment of 1-hydroxy-2-naphthaldehyde with the ylide generated from methyltriphenylphoshonium bromide and n-butyllithium in THF following the conditions described for Example 2a gives 2-[(2-vinyl-1-naphthyl)oxy]but-3-enyl 4-methylbenzenesulfonate.

b) 2H-benzo[h]chromen-2-ylmethyl 4-methylbenzenesulfonate

Treatment of 2-[(2-vinyl-1-naphthyl)oxy]but-3-enyl 4-methylbenzenesulfonate in dichloromethane with bis (tricyclopentylphosphine) benzylidene ruthenium (IV) following the conditions described for Example 1 b provides 2H-benzo[h]chromen-2-ylmethyl 4-methylbenzenesulfonate.

Many variations of the present invention not illustrated herein will occur to those skilled in the art. The present invention is not limited to the embodiments illustrated and described herein, but encompasses all the subject matter within the scope of the appended claims.

What is claimed is:

1. A stereospecific process for preparing a 2-yl chromene derivative comprising:

(a) reacting a 2-hydroxy substituted styrene of formula (I)

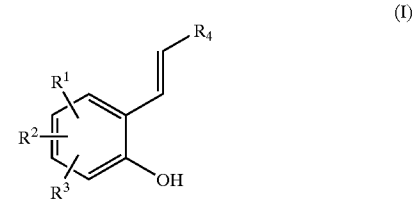

and an optically active 3-hydroxy-1-butene of formula (II)

to form an optically active diene of formula (III)

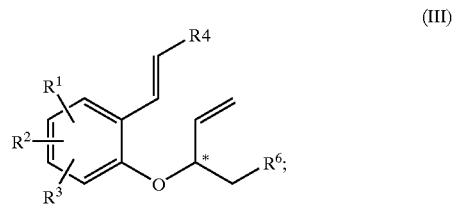

wherein R is a leaving group or a protected oxygen group,
wherein $R^1$, $R^2$ and $R^3$ are independently selected from hydrogen, a halogen atom, a cyano, azido, nitro, hydroxyl, carboxyl, acyl or carboxamido group, a $C_1$ to $C_6$ alkyl group, a 5- to 7-membered aromatic group optionally having as ring members up to 2 heteroatoms independently selected from O, N or S, a $C_5$ to $C_7$ membered aryloxy group, a $C_1$ to $C_6$ alkoxy group, alkanamido group having 1 to 6 carbon atoms in the alkyl chain, alkanesulfonamido group having 1 to 6 carbon atoms in the alkyl chain, an alkanoyloxy group having 1 to 6 carbon atoms in the alkyl chain, a perhalogenated $C_1$ to $C_6$ alkyl or alkoxy group, an amino group or a mono- or di-alkylamino having 1 to 6 carbon atoms per alkyl chain, or two of $R^1$, $R^2$ or $R^3$, taken together, form a 5- to 7-membered saturated or aromatic carbocyclic or bridged carbocyclic ring, wherein the ring may i) optionally have up to two ring atoms selected from S, N, or O, ii) optionally have as a ring member up to 2 carbonyl groups or iii) optionally be substituted by 1 to 2 $R^5$ substituents where each $R^5$ substituent is independently selected from a halogen atom, a cyano, nitro or hydroxyl group, a $C_1$–$C_6$ alkyl group, a $C_1$–$C_6$ alkoxy group, a $C_3$–$C_6$ cycloalkyl group, a 5- to 7-membered aromatic group optionally having 1–2 ring atoms selected from N, O or S, or in spiro form a carbocyclic ring having 5 to 7 carbon atoms, or any combination of i), ii), or iii), wherein $R^4$ is H or a $C_1$–$C_6$ alkyl group, and wherein $R^6$ is a hydroxyl group, a protected oxygen group, or a leaving group; and (b) subjecting the diene of formula (III) to a ring closing metathesis polymerization reaction in the presence of a catalyst to stereospecifically produce an optically active 2-yl chromene derivative of formula (IV)

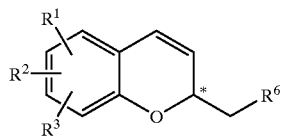

(IV)

wherein $R^1$, $R^2$, $R^3$ and $R^6$ are defined as in formula (III).

2. The process of claim 1 further comprising hydrogenating the 2-yl chromene derivative to form a 2-yl chroman derivative of formula (V)

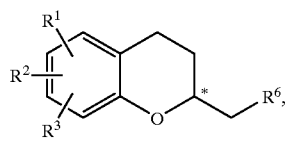

(V)

wherein $R^1$, $R^2$, $R^3$ and $R^6$ are defined as in claim 1.

3. The process of claim 2 wherein $R^4$ is H and the 2-hydroxy substituted styrene of formula (I) is formed by olefination of a salicylaldehyde of the formula (a 1)

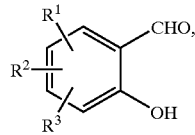

(a1)

wherein $R^1$, $R^2$ and $R^3$ are defined as in claim 1.

4. The process of claim 2 wherein $R^4$ is methyl and the 2-hydroxy substituted styrene of formula (I) is formed by i) reacting a phenol of formula (a2)

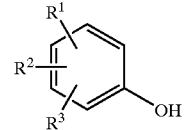

(a2)

and an allylhalide in the presence of a base to form an allyl ether and performing a Claisen rearrangement on the allyl ether to form a 2-[1-propenyl]phenol of the formula (c2)

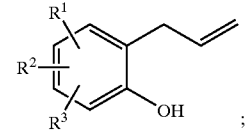

(c2)

and ii) isomerizing the terminal double bond of the 2-[1-propenyl]phenol, wherein $R^1$, $R^2$ and $R^3$ are defined as in claim 2.

5. The process of claim 2 wherein the 2-yl chroman derivative of formula (V) is further reacted to form a 2-aminomethyl-chroman compound or an azaheterocyclyl-methylchroman compound.

6. The process of claim 2 wherein R is a protected oxygen group.

7. The process of claim 1 wherein $R^4$ is H and the 2-hydroxy substituted styrene of formula (I) is formed by olefination of a salicylaldehyde of the formula (a1)

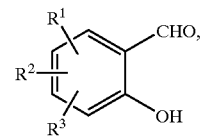

(a1)

wherein $R^1$, $R^2$ and $R^3$ are defined as in claim 1.

8. The process of claim 1 wherein $R^4$ is methyl and the hydroxy substituted styrene of formula (I) is formed by i) reacting a phenol of formula (a2)

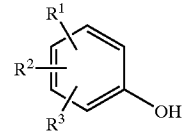

(a2)

and an allylhalide in the presence of a base to form an allyl ether and performing a Claisen rearrangement on the allyl ether to form a 2-[1-propenyl]phenol of the formula (c2)

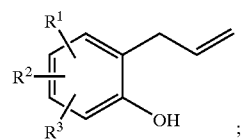

(c2)

and ii) isomerizing the terminal double bond of the 2-[1-propenyl]phenol, wherein $R^1$, $R^2$ and $R^3$ are defined as in claim 1.

9. The process of claim 1 wherein R is a protected oxygen group.

10. The process of claim 1 wherein the protected oxygen group or leaving group is selected from alkyl or aryl sulphonates; halides; alkyl ethers; aryl ethers; silyl ethers; or alkyl or aryl esters.

11. The process of claim 1 wherein the 3-hydroxy-1-butene of formula (II) has an enantiomer excess of at least about 95%.

12. A stereospecific process for preparing a 2-yl-chroman derivative comprising:

(a) olefinating a salicylaldehyde of the formula

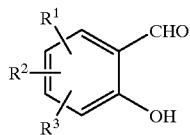

to produce a 2-hydroxystyrene of the formula

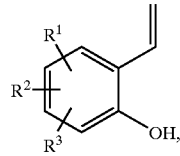

wherein $R^1$, $R^2$ and $R^3$ are independently selected from hydrogen, a halogen atom, a cyano, azido, nitro, hydroxyl, carboxyl, acyl or carboxamido group, a $C_1$ to $C_6$ alkyl group, a 5- to 7-membered aromatic group optionally having as ring members up to 2 heteroatoms independently selected from O, N or S, a $C_5$ to $C_7$ membered aryloxy group, a $C_1$ to $C_6$ alkoxy group, alkanamido group having 1 to 6 carbon atoms in the alkyl chain, alkanesulfonamido group having 1 to 6 carbon atoms in the alkyl chain, an alkanoyloxy group having 1 to 6 carbon atoms in the alkyl chain, a perhalogenated $C_1$ to $C_6$ alkyl or alkoxy group, an amino group or a mono- or di-alkylamino having 1 to 6 carbon atoms per alkyl chain, or two of $R^1$, $R^2$ or $R^3$, taken together, form a 5- to 7-membered saturated or aromatic carbocyclic or bridged carbocyclic ring, wherein the ring may i) optionally have up to two ring atoms selected from S, N, or O, ii) optionally have as a ring member up to 2 carbonyl groups or iii) optionally be substituted by 1 to 2 $R^5$ substituents where each $R^5$ substituent is independently selected from a halogen atom, a cyano, nitro or hydroxyl group, a $C_1$–$C_6$ alkyl group, a $C_1$–$C_6$ alkoxy group, a $C_3$–$C_6$ cycloalkyl group, a 5- to 7-membered aromatic group optionally having 1–2 ring atoms selected from N, 0 or S, or in spiro form a carbocyclic ring having 5 to 7 carbon atoms, or any combination of i), ii), or iii);

(b) reacting the 2-hydroxystyrene and an optically active 3-hydroxy-1-butene of formula (II)

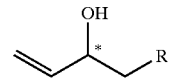

(II)

under Mitsunobu reaction conditions to form a diene of the formula

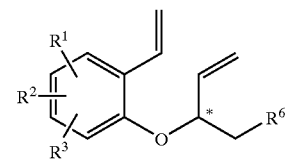

wherein R is a protected oxygen group or leaving group and $R^6$ is a hydroxyl group, protected oxygen group or leaving group;

(c) subjecting the diene to a ring closing metathesis polymerization in the presence of a catalyst, to stereospecifically produce an optically active 2-yl chromene derivative of the formula (IV)

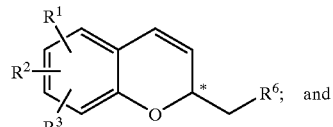

(IV)

(d) hydrogenating the chromene to form a 2-yl chroman derivative of formula (V),

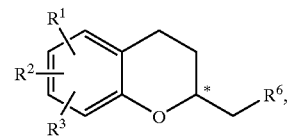

(V)

wherein $R^6$, $R^1$, $R^2$ and $R^3$ are defined as in formula (IV).

13. The process of claim 12 wherein R is a protected oxygen group.

14. The process of claim 12 wherein the protected oxygen group or leaving group is selected from alkyl or aryl sulphonates; halides; alkyl ethers; aryl ethers; silyl ethers; or alkyl or aryl esters.

15. The process of claim 12 wherein the 3-hydroxy-1-butene of formula (II) has an enantiomer excess of at least about 95%.

16. The process of claim 12 wherein the chroman of formula (V) is further reacted to form a 2-aminomethyl-chroman compound or an azaheterocyclylmethylchroman compound.

17. A stereospecific process for preparing a 2-yl chroman derivative comprising:

(a) reacting a phenol of the formula

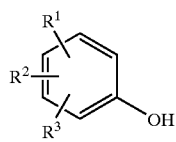

and an allylhalide in the presence of a base to form an allyl ether and performing a Claisen rearrangement on the allyl ether to form a 2-[1-propenyl]phenol of the formula

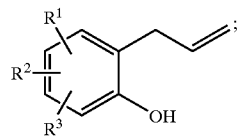

wherein R¹, R² and R³ are independently selected from hydrogen, a halogen atom, a cyano, azido, nitro, hydroxyl, carboxyl, acyl or carboxamido group, a C₁ to C₆ alkyl group, a 5- to 7-membered aromatic group optionally having as ring members up to 2 heteroatoms independently selected from O, N or S, a C₅ to C₇ membered aryloxy group, a C₁ to C₆ alkoxy group, alkanamido group having 1 to 6 carbon atoms in the alkyl chain, alkanesulfonamido group having 1 to 6 carbon atoms in the alkyl chain, an alkanoyloxy group having 1 to 6 carbon atoms in the alkyl chain, a perhalogenated C₁ to C₆ alkyl or alkoxy group, an amino group or a mono- or di-alkylamino having 1 to 6 carbon atoms per alkyl chain, or two of R¹, R² or R³, taken together, form a 5- to 7-membered saturated or aromatic carbocyclic or bridged carbocyclic ring, wherein the ring may I) optionally have up to two ring atoms selected from S, N, or O, ii) optionally have as a ring member up to 2 carbonyl groups or iii) optionally be substituted by 1 to 2 R⁵ substituents where each R⁵ substituent is independently selected from a halogen atom, a cyano, nitro or hydroxyl group, a C₁–C₆ alkyl group, a C₁–C₆ alkoxy group, a C₃–C₆ cycloalkyl group, a 5- to 7-membered aromatic group optionally having 1–2 ring atoms selected from N, O or S, or in spiro form a carbocyclic ring having 5 to 7 carbon atoms, or any combination of I), ii), or iii);

(c) isomerizing the terminal propenyl double bond of the 2-[1-propenyl]phenol to produce a 2-[2-propenyl]phenol of the formula

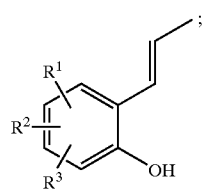

(d) reacting the 2-[2-propenyl]phenol with an optically active 3-hydroxy-1-butene of formula (II)

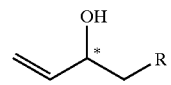

under Mitsunobu reaction conditions to provide a diene of the formula

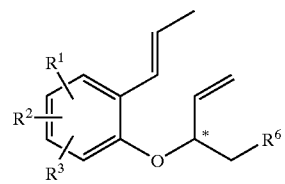

wherein R is a protected oxygen group or leaving group, and R⁶ represents a hydroxyl group, a protected oxygen group or a leaving group;

(e) subjecting the diene to a ring closing metathesis polymerization in the presence of a catalyst to stereospecifically produce an optically active 2-yl chromene derivative of the formula (IV)

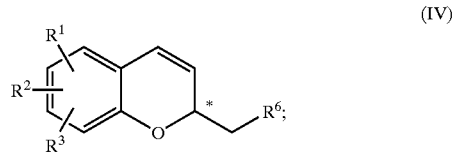

and (f) hydrogenating the chromene derivative to form a 2-yl chroman derivative of formula (V)

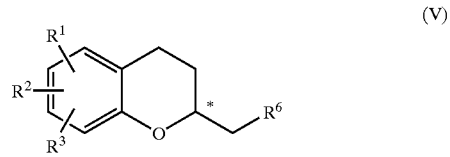

wherein R¹, R², R³ and R⁶ are defined as in formula (IV).

18. The process of claim 17 wherein R is a protected oxygen group.

19. The process of claim 17 wherein the protected oxygen group or leaving group is selected from alkyl or aryl sulphonates; halides; alkyl ethers; aryl ethers; silyl ethers; or alkyl or aryl esters.

20. The process of claim 17 wherein the 3-hydroxy-1-butene of formula (II) has an enantiomer excess of at least about 95%.

21. The process of claim 17 wherein the chroman of formula (V) is further reacted to form a 2-aminomethyl-chroman compound or an azaheterocyclylmethylchroman compound.

22. The process of claim 1 wherein the 3-hydroxy-1-butene of formula (II) has an enantiomer excess of at least about 30%.

23. The process of claim 1 wherein the 3-hydroxy-1-butene of formula (II) has an enantiomer excess of at least about 50%.

* * * * *